(12) United States Patent
Moser et al.

(10) Patent No.: US 8,658,861 B2
(45) Date of Patent: Feb. 25, 2014

(54) PEA CULTIVAR FP2291

(75) Inventors: Paul Moser, Boise, ID (US); Roxanne Mainz, Stanton, MN (US)

(73) Assignee: Agra Plus, Inc., Eagle, ID (US)

( * ) Notice: Subject to any disclaimer, the term of this patent is extended or adjusted under 35 U.S.C. 154(b) by 107 days.

(21) Appl. No.: 13/330,541

(22) Filed: Dec. 19, 2011

(65) Prior Publication Data

US 2012/0216306 A1 Aug. 23, 2012

Related U.S. Application Data

(60) Provisional application No. 61/425,722, filed on Dec. 21, 2010.

(51) Int. Cl.
- *A01H 5/00* (2006.01)
- *A01H 5/10* (2006.01)
- *A01H 4/00* (2006.01)
- *A01H 1/00* (2006.01)
- *C12N 15/82* (2006.01)

(52) U.S. Cl.
USPC ........... 800/298; 435/415; 435/426; 435/421; 800/260; 800/278; 800/288; 800/279

(58) Field of Classification Search
None
See application file for complete search history.

(56) References Cited

U.S. PATENT DOCUMENTS

| 7,554,010 | B1 | 6/2009 | Moser |
| 7,714,196 | B1 * | 5/2010 | Webster ........................ 800/298 |

OTHER PUBLICATIONS

Moser, Paul, U.S. Appl. No. 13/330,512, filed Dec. 19, 2011, titled "PEA CULTIVAR FP2292", 29 pages.
Mainz, Roxanne, Unpublished U.S. Appl. No. 13/330,483, filed Dec. 19, 2011, titled "PEA CULTIVAR FP2311", 28 pages.
Non Final Office Action received for U.S. Appl. No. 13/330,512 mailed on Jul. 5, 2013, 8 pages.
Non Final Office Action received for U.S. Appl. No. 13/330,463, mailed on Jul. 9, 2013, 11 pages.

* cited by examiner

*Primary Examiner* — Stuart F Baum
(74) *Attorney, Agent, or Firm* — Morrison & Foerster LLP

(57) ABSTRACT

A novel pea cultivar designated FP2291 is disclosed. The invention relates to the seeds of pea cultivar FP2291, to the plants of pea cultivar FP2291, and parts thereof, for example pollen, ovule, berry or pod. The invention also relates to methods for producing a pea plant by crossing the cultivar FP2291 with itself or another pea line. The invention further relates to methods for producing a pea plant containing in its genetic material one or more transgenes and to the transgenic plants produced by that method and to methods for producing other pea lines derived from the pea cultivar FP2291.

20 Claims, No Drawings

PEA CULTIVAR FP2291

CROSS REFERENCE TO RELATED APPLICATIONS

This application claims the benefit of U.S. Provisional Application No. 61/425,722, filed Dec. 21, 2010, which is hereby incorporated by reference in its entirety.

FIELD OF THE INVENTION

The present invention relates to a new and distinctive Pea cultivar (*Pisum sativum*), designated FP2291.

BACKGROUND OF THE INVENTION

Pea, *Pisum sativum*, is an important and valuable vegetable crop. There is a continuing need to develop stable, high yielding pea cultivars that are agronomically sound and that maximize the amount of yield produced on the land.

SUMMARY OF THE INVENTION

The present invention meets these needs by providing an improved pea cultivar with smaller sieve average, higher root rot tolerance, and resistance to powdery mildew and pea enation mosaic virus. According to the invention, there is provided a novel pea cultivar designated FP2291 having ATCC Accession Number PTA-12690. This invention thus relates to the seeds, plants, and parts thereof, for example pollen, ovule, berry or pod of pea cultivar FP2291 having ATCC Accession Number PTA-12690. The invention also relates to methods for producing a pea plant produced by crossing the pea FP2291 having ATCC Accession Number PTA-12690 with itself or another pea line, to methods for producing a pea plant containing in its genetic material one or more transgenes, and to the transgenic pea plants produced by that method. This invention also relates to methods for producing other pea cultivars derived from pea cultivar FP2291 having ATCC Accession Number PTA-12690 and to the pea cultivar derived by the use of those methods. This invention further relates to hybrid pea seeds and plants produced by crossing the line FP2291 having ATCC Accession Number PTA-12690 with another pea line.

The invention is also directed to a method of producing a pod or a berry comprising growing a plant according to the instant invention to produce a pod, and harvesting said pod. In one embodiment, the method further comprises processing the pod to obtain a berry. In one embodiment, a berry according the instant invention is a fresh product, a canned product or a frozen product.

The invention is also directed to a method of producing a berry comprising obtaining a pod of a plant according to the instant invention and processing the pod to obtain a berry. In one embodiment, a berry according the instant invention is a fresh produce, a canned product or a frozen product.

In another aspect, the present invention provides regenerable cells for use in tissue culture of pea cultivar FP2291 having ATCC Accession Number PTA-12690. The tissue culture will preferably be capable of regenerating plants having the physiological and morphological characteristics of the foregoing pea plant, and of regenerating plants having substantially the same genotype as the foregoing pea plant. Preferably, the regenerable cells in such tissue cultures will be embryos, protoplasts, seeds, callus, pollen, leaves, anthers, roots, and meristematic cells. Still further, the present invention provides pea plants regenerated from the tissue cultures of the invention.

Another objective of the invention is to provide methods for producing other pea plants derived from pea cultivar FP2291 having ATCC Accession Number PTA-12690. Pea cultivars derived by the use of those methods are also part of the invention.

The invention also relates to methods for producing a pea plant containing in its genetic material one or more transgenes and to the transgenic pea plant produced by that method.

In another aspect, the present invention provides for gene converted plants of FP2291 having ATCC Accession Number PTA-12690. The at least one transferred gene may preferably be a dominant or recessive allele. Preferably, the at least one transferred gene will confer such traits as male sterility; herbicide resistance; insect resistance; resistance for bacterial, fungal, or viral disease; male fertility; enhanced nutritional quality; and industrial usage. The single gene may be a naturally occurring pea gene or a transgene introduced through genetic engineering techniques.

The invention further provides methods for developing a pea plant in a pea plant breeding program using plant breeding technique including recurrent selection, backcrossing, pedigree breeding, restriction fragment length polymorphism enhanced selection, genetic marker enhanced selection, and transformation. Seeds, pea plant, and parts thereof produced by such breeding methods are also part of the invention.

DEFINITIONS

In the description and tables which follow, a number of terms are used. In order to provide a clear and consistent understanding of the specification and claims, including the scope to be given such terms, the following definitions are provided:

"Allele"—The allele is any of one or more alternative form of a gene, all of which alleles relates to one trait or characteristic. In a diploid cell or organism, the two alleles of a given gene occupy corresponding loci on a pair of homologous chromosomes.

"Backcrossing"—Backcrossing is a process in which a breeder repeatedly crosses hybrid progeny back to one of the parents, for example, a first generation hybrid F1 with one of the parental genotype of the F1 hybrid.

"Essentially all the physiological and morphological characteristics"—A plant having essentially all the physiological and morphological characteristics means a plant having the physiological and morphological characteristics, except for the characteristics derived from the converted gene.

"Regeneration"—Regeneration refers to the development of a plant from tissue culture.

"Single gene converted"—Single gene converted or conversion plant refers to plants which are developed by a plant breeding technique called backcrossing wherein essentially all of the desired morphological and physiological characteristics of a line are recovered in addition to the single gene transferred into the line via the backcrossing technique or via genetic engineering.

"Maturity Date"—Plants are considered mature when the pods have reached their maximum desirable berry size and sieve size for the specific use intended.

"Determinate Plant"—A determinate plant will grow to a fixed number of nodes while an indeterminate plant will continue to grow during the season. They have a high pod to vine weight ratio.

"Tenderometer"—This is a device for determining the maturity and tenderness of a pea sample.

"Heat unit"—The amount of heat needed to mature a crop. It is used to measure maturity based on the daily accumulated heat produced during the growing season. The formula [(daily maximum F.°–daily minimum F.°)–40]/2 is used to calculate heat units for peas.

"Sieve Size" (sv)—Sieve size measures the diameter of the fresh pea and used in grading peas. A sieve 1 is a berry that goes through a hole 9/32 in. (7.15 mm) in diameter, a sieve 2 berry goes through a hole 10/32 in. (7.94 mm) in diameter, a sieve 3 berry goes through a hole 11/32 in. (10.32 mm) in diameter, a sieve 4 berry goes through a hole 12/32 in. (9.53 mm), a sieve 5 berry goes through a hole 13/32 in. (10.32 mm), and a sieve 6 and above berry goes through a hole greater than 13/32 in. (10.32 mm). A sieve size average is calculated by multiplying the percent of peas within each sieve size by the sieve size, summing these products and dividing by 100.

"Pea Yield" (Tons/Acre)—The yield in tons/acre is the actual yield of the peas at harvest.

"Plant Height"—Plant height is taken from the top of soil to top most leaf of the plant and is measured in centimeters.

"Field holding ability"—A pea plant that has field holding ability means a plant having berries that slowly change tenderometer over time. Few peas have much field holding ability.

"Machine harvestable plant"—A machine harvestable plant means a pea plant that stands enough to allow pods and berries to be harvested by machine. The pods can be removed by a machine from the plant without leaves and other plant parts being harvested.

"Plant adaptability"—A plant having a good plant adaptability means a plant that will perform well in different growing conditions and seasons.

"Afila"—Afila is a foliar configuration resulting from the gene 'af'. It acts to transform the leaflets on a normal foliage pea to tendrils. Afila plants tend to be more upright in the field than normal foliage peas as the tendrils grab onto one another to hold each other up.

"Nodes to 1$^{st}$ flower"—This is obtained by counting the node above the point of cotyledon attachment to the node from which the first peduncle arises.

"Peduncle"—A peduncle is the stalk that bearing flower(s) and subsequent pod(s) arising from a node.

"Node"—A node is the thickened enlargement on a plant. It is where the stipules, leaf, and peduncle arise.

"Stipules"—A pair of leaf like appendages borne at the base of each pea leaf or stalk.

"RHS"—RHS refers to the Royal Horticultural Society of England which publishes an official botanical color chart quantitatively identifying colors according to a defined numbering system. The chart may be purchased from Royal Hort Society Enterprise Ltd RHS Garden; Wisley, Woking; Surrey GU236QB, UK.

DETAILED DESCRIPTION OF THE INVENTION

According to the invention, there is provided a novel pea cultivar designated FP2291. The pea cultivar FP2291 is an afila pea with a smaller sieve size average. It has resistance to powdery mildew, good resistance to pea enation mosaic virus and intermediate resistance to the root rot complex that consists of a number of organisms, including *Aphpnomyces euteiches*, *Fusarium solani*, *Rhizotonia solani*, and *Pythium ultimum*. Unlike most current varieties of pea, pea cultivar FP2291 can be grown in land that has some root rot problems or in land without root rot pressure. Further, none of the current varieties have the combination of root rot tolerance, quality with a smaller sieve average, and resistance to powdery mildew and enation mosaic resistance that pea cultivar FP2291 has.

Pea cultivar FP2291 is derived from the hand pollinated cross between Syngenta breeding lines Gallant and HP2486-16-4-1. Using the pedigree method of selection, singles were selected in the F2 and F3 generation. It was bulk harvested in F4 and again in the F5 generations. From F5 generation pea cultivar FP2291 was bulked harvested to provide seed for further increases. Pea cultivar FP2291 has been uniform and stable for seven generations since the F5 harvest.

Pea cultivar FP2291 is a garden pea cultivar suitable for processing markets. It can be compared to the variety Gallant from Syngenta Seeds, Inc. Pea cultivar FP2291 statistically differs from Gallant in the following traits.

Pea cultivar FP2291 and Gallant are statistically different in final plant height. In trials located in Minnesota and Idaho during Year 1, pea cultivar FP2291 was taller than Gallant. In Minnesota, pea cultivar FP2291 averaged 47 cm in final plant height and Gallant averaged 39 cm in final plant height. In Idaho, pea cultivar FP2291 and Gallant average final plant height was 57 and 53 cm, respectively.

The above values for final plant height are based on average measurements from Minnesota and Idaho collected during the growing season of Year 1. Twenty plants of each cultivar were measured final plant height. Each plot was comprised of 800 plants in Minnesota and 100 plants in Idaho. All statistical computations were carried out using Statistix 8.0 (Analytical Software, Tallahassee Fla.). The analysis is shown in detail in the Examples below (Tables 1-5).

At maturity, the first bloom of a plant of pea cultivar FP2291 is at the 14th node and a plant of pea cultivar FP2291 reaches maturity after 64 to 65 days for processing. Based on data collected in Idaho and Minnesota and averaged together in Year 1, plants of pea cultivar FP2291 typically reach a height of about 52 cm. This is about 6 cm taller than Gallant and 8 cm shorter than the cultivar Wando. Based on data collected in Idaho and Minnesota in Year 1, pea cultivar FP2291 is a determinate cultivar, without branching. Its plants typically have 17-19 nodes of the zig-zag type. It has medium stockiness and its leaflets type is leafless (afila). Stipules are present and clasping, marbled (like Alaska) and dark green. The stipules are medium sized. Regarding the flower color, the venation is pale green, the standard is white, the wing is white and the keel is greenish.

Based on data collected in Idaho and Minnesota in Year 1, the pods of pea cultivar FP2291 have a straight shape, and are slightly pointed at the end. The pods' color is dark green (like Alderman), their surface smooth and dull, and they are primarily double pods at a node. The berries of pea cultivar FP2291 have a medium green color. The average sieve size is 3.4 with the percent distribution being—<7.1 mm—1 sieve: 2%; 7.1-7.9 mm—2 sieve: 18%; 7.9-8.7 mm—3 sieve: 28%; 8.7-9.5 mm—4 sieve: 41%; 9.5-10.3 mm—5 sieve: 12%; 10.3>—6 sieve: 0%.

Based on data collected in Minnesota in Year 1, when dry-mature, the shape of the seeds is somewhat flattened, the surface wrinkled, and the color pattern and primary color is a bicolor of cream and green. The color of the hilum is tan, the color of the cotyledon is green. The weight of 100 seeds is about 18 grams.

Plants of pea cultivar FP2291 are resistant to powdery mildew, races 1 and 2 fusarium wilt, and pea cultivar FP2291 is moderately resistant to root rot complex.

This invention also is directed to methods for producing a pea plant by crossing a first parent pea plant with a second parent pea plant wherein either the first or second parent pea plant is a pea plant of the line FP2291. Still further, this invention also is directed to methods for producing a cultivar FP2291-derived pea plant by crossing cultivar FP2291 with a second pea plant and growing the progeny seed, and repeating the crossing and growing steps with the cultivar FP2291-derived plant from 0 to 7 times. Thus, any such methods using the cultivar FP2291 are part of this invention: selfing, backcrosses, hybrid production, crosses to populations, and the like. All plants produced using cultivar FP2291 as a parent are within the scope of this invention, including plants derived from cultivar FP2291. Advantageously, the cultivar is used in crosses with other, different, cultivars to produce first generation (F1) pea seeds and plants with superior characteristics.

As used herein, the term "plant" includes plant cells, plant protoplasts, plant cell tissue cultures from which pea plants can be regenerated, plant calli, plant clumps, and plant cells that are intact in plants or parts of plants, such as embryos, pollen, ovules, flowers, seeds, pods, stems, roots, anthers, and the like.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed pea plants, using transformation methods as described below to incorporate transgenes into the genetic material of the pea plant(s).

Expression Vectors for Pea Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983), Aragao F. J. L., et al., Molecular Breeding 4:6 491499 (1998). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986).

Other selectable marker genes confer resistance to herbicides such as glyphosate, glufosinate, or broxynil. Comai et al., Nature 317:741-744 (1985), Gordon-Kamm et al., Plant Cell 2:603-618 (1990) and Stalker et al., Science 242:419-423 (1988), Saker M. M., et al, Biologia Plantarum 40:4 507-514 (1998), Russel, D. R, et al, Plant Cell Report 12:3 165-169 (1993).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., Plant Mol. Biol. Rep. 5:387 (1987), Teeri et al., EMBO 1. 8:343 (1989), Koncz et al., Proc. Natl. Acad. Sci U.S.A. 84:131 (1987), DeBlock et al., EMBO J. 3:1681 (1984), Grossi M. F., et al., Plant Science 103:2 189-198 (1994), Lewis M. E., Journal of the American Society for Horticultural Science 119:2 361-366 (1994), Zhang et al., Journal of the American Society for Horticultural Science 122:3 300-305 (1997).

Recently, in vivo methods for visualizing GUS activity that do not require destruction of plant tissue have been made available. Molecular Probes publication 2908, Imagene Green_, p. 1-4 (1993) and Naleway et al., J. Cell Biol. 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263: 802 (1994). GFP and mutants of GFP may be used as screenable markers.

Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in pea. Optionally, the inducible promoter is operably linked to a nucleotide sequence encoding a signal sequence which is operably linked to a gene for expression in pea. With an inducible promoter the rate of transcription increases in response to an inducing agent. Any inducible promoter can be used in the instant invention. See Ward et al., Plant Mol. Biol. 22:361-366 (1993). Exemplary inducible promoters include, but are not limited to, that from the ACEI system, which responds to copper (Meft et al., PNAS 90:4567-4571 (1993)); In2 gene from maize, which responds to benzenesulfonamide herbicide safeners (Hershey et al., Mol. Gen Genetics 227:229-237 (1991) and Gatz et al., Mol. Gen. Genetics 243:32-38 (1994)); or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in pea or the constitutive promoter is operably linked to a nucleotide sequence encoding a signal sequence which is operably linked to a gene for expression in pea.

Many different constitutive promoters can be utilized in the instant invention. Exemplary constitutive promoters include, but are not limited to, the promoters from plant viruses such as the 35S promoter from CaMV (Odell et al., Nature 313:810-812 (1985), Aragao et al., Genetics and Molecular Biology 22:3, 445-449 (1999)); and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO 1. 3:2723-2730 (1984)); and maize H3 histone (Lepetit et al., Mol. Gen. Genetics 231:276-285 (1992) and Atanassova et al., Plant Journal 2 (3):291-300 (1992)). The ALS promoter, Xbal/Ncol fragment 5' to the Brassica napus ALS3 structural gene (or a nucleotide sequence similar to said Xbal/Ncol fragment), represents a particularly useful constitutive promoter. See PCT application WO96/30530.

C. Tissue-Specific or Tissue-Preferred Promoters

A tissue-specific promoter is operably linked to a gene for expression in pea. Optionally, the tissue-specific promoter is operably linked to a nucleotide sequence encoding a signal sequence which is operably linked to a gene for expression in pea. Plants transformed with a gene of interest operably linked to a tissue-specific promoter produce the protein product of the transgene exclusively, or preferentially, in a specific tissue. Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an antherspecific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)); or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is pea. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium falvum*); Martin et al., Science 262:1432 (1993) (tomato Pto gene for resistance to *Pseudomonas syringae* pv. Tomato encodes a protein kinase); Mindrinos et al., Cell 78:1089 (1994) (Arabidopsis RSP2 gene for resistance to *Pseudomonas syingae*).

B. A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding deltaendotoxin genes can be purchased from American Type Culture Collection, Manassas, Va., for example, under ATCC Accession Nos. 40098, 67136, 31995, and 31998.

C. A lectin. See, for example, Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262: 16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116: 165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative, or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104: 1467 (1994), who provide the nucleotide sequence of a maize calmodulin cDNA clone.

L. A hydrophobic moment peptide. See PCT application W095/16776 (disclosure of peptide derivatives of Tachyplesin which inhibit fungal plant pathogens) and PCT application W095/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10:1436 (1992). The cloning and characterization of a gene which encodes a bean endopolygalacturonase-inhibiting protein is described by Toubart et al., Plant 1. 2:367 (1992).

R. A development-arrestive protein produced in nature by a plant. For example, Logemann et al., Biol/Technology 10:305 (1992), have shown that transgenic plants expressing the barley ribosome-inactivating gene have an increased resistance to fungal disease.

2. Genes that Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appi. Genet. 80:449 (1990), respectively.

B. Glyphosate (resistance impaired by mutant 5-enolpyruvl-3-phosphikimate synthase (EPSP) and aroA genes, respectively) and other phosphono compounds such as gluphosinate (phosphinothricin acetyl transferase, PAT, and *Streptomyces hygroscopicus* phosphinothricinacetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. See also Russel, D. R., et al, Plant Cell Report 12:3 165-169 (1993). The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2, and Acc1-S3 genes described by Marshall et al., Theor. Appl. Genet. 83:435 (1992).

C. A herbicide that inhibits photosynthesis, such as a triazine (psbA and gs+genes) and a benzonitrile (nitrilase gene). Przibilla et al., Plant Cell 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285: 173 (1992).

3. Genes that Confer or Contribute to a Value-Added Trait, Such as:

A. Delayed and attenuated symptoms to Bean Golden Mosaic Geminivirus (BGMV), for example by transforming a plant with antisense genes from the Brazilian BGMV. See Arago et al., Molecular Breeding. 1998, 4: 6, 491-499.

B. Increased the pea content in Methionine by introducing a transgene coding for a Methionine rich storage albumin (2S-albumin) from the Brazil nut as described in Arago et al., Genetics and Molecular Biology. 1999, 22: 3, 445-449.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227: 1229 (1985). McClean, P., et al. Plant Cell Tissue Org. Cult. 24(2, February), 131-138 (1991), Lewis et al., Journal of the American Society for Horticultural Science, 119:2, 361-366 (1994), Zhang, Z., et al. 1. Amer. Soc. Hort. Sci. 122(3): 300-305 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10: 1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Despite the fact the host range for *Agrobacterium*-mediated transformation is broad, some major cereal or vegetable crop species and gymnosperms have generally been recalcitrant to this mode of gene transfer, even though some success has recently been achieved in rice and corn. Hiei et al., The Plant Journal 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 mls which is sufficient to penetrate plant cell walls and membranes. Russell, D. R., et al. Pl. Cell. Rep.

12(3, January), 165-169 (1993), Aragao, F. J. L., et al. Plant Mol. Biol. 20(2, October), 357-359 (1992), Aragao Theor. Appl. Genet. 93:142-150 (1996), Kim, J.; Minamikawa, T. Plant Science 117: 131-20 138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome or spheroplast fusions have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draperetal., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, P 53 (1990); D'Halluin et al., Plant Cell 4:1495-1505 (1992) and Spencer et al., Plant Mol. Biol. 24:51-61 (1994).

Following transformation of pea target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic pea line. Alternatively, a genetic trait which has been engineered into a particular pea cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term pea plant, cultivar or pea line is used in the context of the present invention, this also includes any single gene conversions of that cultivar or line. The term "single gene converted plant" as used herein refers to those pea plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental pea plants for that line. The parental pea plant which contributes the gene for the desired characteristic is termed the nonrecurrent or donor parent. This terminology refers to the fact that the nonrecurrent parent is used one time in the backcross protocol and therefore does not recur. The parental pea plant to which the gene or genes from the nonrecurrent parent are transferred is known as the recurrent parent as it is used for several rounds in the backcrossing protocol (Poehlman & Sieper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a pea plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic. Examples of these traits include, but are not limited to, herbicide resistance (such as bar or pat genes), resistance for bacterial, fungal, or viral disease (such as gene I used for BCMV resistance), insect resistance, enhanced nutritional quality (such as 2s albumine gene), industrial usage, agronomic qualities (such as the "persistent green gene"), yield stability, and yield enhancement. These genes are generally inherited through the nucleus. Some other single gene traits are described in U.S. Pat. Nos. 5,777,196; 5,948,957; and 5,969,212, the disclosures of which are specifically hereby incorporated by reference.

EXAMPLES

In the tables that follow, the traits and characteristics of pea cultivar FP2291 are given along with data on cultivar Gallant used as a check.

TABLE 1

Explanation of statistical analysis variables used in the following examples

FPFNID06 = FP2291, Final Node, Idaho, Year 1
GAFNID06 = Gallant, Final Node, Idaho, Year 1
FPPDLID06 = FP2291, Pod Length, Idaho, Year 1
GAPDLID06 = Gallant, Pod Length, Idaho, Year 1
FPFNMN06 = FP2291, Final Node, Minnesota, Year 1
GAFNMN06 = Gallant, Final Node, Minnesota, Year 1
FPPDLMN06 = FP2291, Pod Length, Minnesota, Year 1
GAPDLMN06 = Gallant, Pod Length, Minnesota, Year 1

AOV: analysis of variants
DF: degree of freedom
SS: sum of squares
MS: mean of squares
F: F-distribution
P: probability distribution

TABLE 2

| Descriptive Statistics: One-Way AOV for: FPFNID06 GAFNID06 | | | | | |
|---|---|---|---|---|---|
| Variable | N | Mean | SD | Minimum | Maximum |
| FPFNID06 | 20 | 19.600 | 1.6983 | 17.000 | 23.000 |
| GAFNID06 | 20 | 18.100 | 1.5526 | 15.00 | 20.000 |
| Source | DF | SS | MS | F | P |
| Between | 1 | 22.500 | 22.5000 | 8.50 | 0.0059 |
| Within | 38 | 100.600 | 2.6474 | | |
| Total | 39 | 123.100 | | | |
| Grand Mean 18.850 | | | | CV 8.63 | |

| | Chi-Sq | DF | P |
|---|---|---|---|
| Bartlett's Test of Equal Variances | 0.15 | 1 | 0.6997 |
| Cochran's Q | | 0.5447 | |
| Largest Var/Smallest Var | | 1.1965 | |
| Component of variance for between groups | | 0.99263 | |
| Effective cell size | | 20.0 | |

| Variable | Mean |
|---|---|
| FPFNID06 | 19.600 |
| GAFNID06 | 18.100 |
| Observation per Mean | 20 |
| Standard Error of a Mean | 0.3638 |
| Std Error (Diff of 2 Means) | 0.5145 |

| LSD All-Pairwise Comparisons Test | | | |
|---|---|---|---|
| Variable | | Mean | Homogeneous Groups |
| FPFNID06 | | 19.600 | A |
| GAFNID06 | | 18.100 | B |
| Alpha | 0.05 | Standard Error for Comparison | 0.5145 |
| Critical T Value | 2.024 | Critical Value for Comparison | 1.0416 |

All 2 means are significantly different from one another.

TABLE 3

| Descriptive Statistics: One-Way AOV for: FPPDLID06 GAPDLID06 | | | | | |
|---|---|---|---|---|---|
| Variable | N | Mean | SD | Minimum | Maximum |
| FPPDLID06 | 20 | 8.7450 | 0.4628 | 8.2000 | 10.000 |
| GAPDLID06 | 20 | 8.4550 | 0.4174 | 7.8000 | 9.2000 |
| Source | DF | SS | MS | F | P |
| Between | 1 | 0.84100 | 0.84100 | 4.33 | 0.0442 |
| Within | 38 | 7.37900 | 0.19418 | | |
| Total | 39 | 8.22000 | | | |
| Grand Mean 8.6000 | | | | CV 5.12 | |

| | Chi-Sq | DF | P |
|---|---|---|---|
| Bartlett's Test of Equal Variances | 0.20 | 1 | 0.6568 |
| Cochran's Q | | 0.5515 | |
| Largest Var/Smallest Var | | 1.2296 | |
| Component of variance for between groups | | 0.03234 | |
| Effective cell size | | 20.0 | |

| Variable | Mean |
|---|---|
| FPPDLID06 | 8.7450 |
| GAPDLID06 | 8.4550 |
| Observation per Mean | 20 |
| Standard Error of a Mean | 0.0985 |
| Std Error (Diff of 2 Means) | 0.1393 |

TABLE 3-continued

| | | LSD All-Pairwise Comparisons Test | | |
|---|---|---|---|---|
| Variable | | Mean | Homogeneous Groups | |
| FPPDLID06 | | 8.7450 | A | |
| GAPDLID06 | | 8.4550 | B | |
| Alpha | 0.05 | Standard Error for Comparison | | 0.1393 |
| Critical T Value | 2.024 | Critical Value for Comparison | | 0.2821 |

All 2 means are significantly different from one another.

TABLE 4

| | Descriptive Statistics: One-Way AOV for: FPFNMN06 GAFNMN06 | | | | |
|---|---|---|---|---|---|
| Variable | N | Mean | SD | Minimum | Maximum |
| FPFNMN06 | 20 | 17.650 | 1.0400 | 16.000 | 19.000 |
| GAFNMN06 | 20 | 16.900 | 0.7881 | 16.000 | 19.000 |
| Source | DF | SS | MS | F | P |
| Between | 1 | 5.6250 | 5.62500 | 6.61 | 0.0142 |
| Within | 38 | 32.3500 | 0.85132 | | |
| Total | 39 | 37.9750 | | | |
| Grand Mean 17.275 | | | | CV 5.34 | |

| | Chi-Sq | DF | P |
|---|---|---|---|
| Bartlett's Test of Equal Variances | 1.41 | 1 | 0.2356 |
| Cochran's Q | | 0.6352 | |
| Largest Var/Smallest Var | | 1.7415 | |
| Component of variance for between groups | | 0.23868 | |
| Effective cell size | | 20.0 | |

| Variable | Mean |
|---|---|
| FPFNMN06 | 17.650 |
| GAFNMN06 | 16.900 |
| Observation per Mean | 20 |
| Standard Error of a Mean | 0.2063 |
| Std Error (Diff of 2 Means) | 0.2918 |

| | | LSD All-Pairwise Comparisons Test | | |
|---|---|---|---|---|
| Variable | | Mean | Homogeneous Groups | |
| FPFNMN06 | | 17.650 | A | |
| GAFNMN06 | | 16.900 | B | |
| Alpha | 0.05 | Standard Error for Comparison | | 0.2918 |
| Critical T Value | 2.024 | Critical Value for Comparison | | 0.5907 |

All 2 means are significantly different from one another.

TABLE 5

| | Descriptive Statistics: One-Way AOV for: FPPDLMN06 GAPDLMN06 | | | | |
|---|---|---|---|---|---|
| Variable | N | Mean | SD | Minimum | Maximum |
| FPPDLMN06 | 20 | 5.9625 | 0.5147 | 5.0000 | 7.0000 |
| GAPDLMN06 | 20 | 5.3875 | 0.3759 | 5.0000 | 6.0000 |
| Source | DF | SS | MS | F | P |
| Between | 1 | 3.3063 | 3.30625 | 16.3 | 0.0003 |
| Within | 38 | 7.7187 | 0.20312 | | |
| Total | 39 | 11.0250 | | | |
| Grand Mean 5.6750 | | | | CV 7.94 | |

| | Chi-Sq | DF | P |
|---|---|---|---|
| Bartlett's Test of Equal Variances | 1.80 | 1 | 0.1796 |
| Cochran's Q | | 0.6522 | |
| Largest Var/Smallest Var | | 1.8754 | |

TABLE 5-continued

| Component of variance for between groups | 0.15516 |
|---|---|
| Effective cell size | 20.0 |

| Variable | Mean |
|---|---|
| FPPDLMN06 | 5.9625 |
| GAPDLMN06 | 5.3875 |
| Observation per Mean | 20 |
| Standard Error of a Mean | 0.1008 |
| Std Error (Diff of 2 Means) | 0.1425 |

LSD All-Pairwise Comparisons Test

| Variable | | Mean | Homogeneous Groups | |
|---|---|---|---|---|
| FPPDLMN06 | | 5.9625 | A | |
| GAPDLMN06 | | 5.3875 | B | |
| Alpha | 0.05 | Standard Error for Comparison | | 0.1425 |
| Critical T Value | 2.024 | Critical Value for Comparison | | 0.2885 |

All 2 means are significantly different from one another.

DEPOSIT

Applicants have made a deposit to the public without restriction of at least 2500 seeds of with the American Type Culture Collection (ATCC), Manassas, Va., 20110-2209 U.S.A., with a deposit on Mar. 21, 2012, which has been assigned ATCC Deposit Number PTA-12690. This deposit of the pea cultivar designated FP2291 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Cultivar Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

All references cited herein are incorporated by reference in the instant application in their entireties.

What is claimed is:

1. Seed of pea cultivar designated FP2291, representative seed of said cultivar having been deposited under ATCC Accession Number PTA-12690.

2. A pea plant, or a part thereof, produced by growing the seed of claim 1.

3. Pollen of the plant of claim 2.

4. An ovule of the plant of claim 2.

5. A pod or a berry of the plant of claim 2.

6. A tissue culture of regenerable cells of a plant of pea cultivar designated FP2291, wherein the tissue regenerates plants having all the morphological and physiological characteristics of a plant of pea cultivar designated FP2291, representative seeds having been deposited ATCC Accession Number PTA-12690.

7. The tissue culture of claim 6, wherein the regenerable cells are produced from meristematic cells, leaves, pollen, embryo, protoplasts, callus, root, root tips, stems, anther, flowers, seeds, or pods.

8. A pea plant regenerated from the tissue culture of claim 6, wherein the regenerated plant has all the morphological and physiological characteristics of a plant of pea cultivar designated FP2291, representative seeds having been deposited under ATCC Accession Number PTA-12690.

9. A method for producing a hybrid pea seed comprising crossing a first parent pea plant with a second parent pea plant and harvesting the resultant hybrid pea seed, wherein said first or second parent pea plant is the pea plant of claim 2.

10. A method of producing an herbicide resistant pea plant comprising transforming the pea plant of claim 2 with at least one transgene that confers herbicide resistance.

11. An herbicide resistant pea plant produced by the method of claim 10.

12. The pea plant of claim 11, wherein the pea plant comprises at least one transgene that confers resistance to at least one herbicide selected from the group consisting of imidazolinone, sulfonylurea glyphosate, glufosinate, Lphosphinothricin, triazine, and benzonitrile.

13. A method of producing an insect resistant pea plant comprising transforming the pea plant of claim 2 with at least one transgene that confers insect resistance.

14. An insect resistant pea plant produced by the method of claim 13.

15. The pea plant of claim 14, wherein the pea plant comprises a transgene encoding a *Bacillus thuringiensis* protein.

16. A method of producing a disease resistant pea plant comprising transforming the pea plant of claim 2 with at least one transgene that confers resistance to bacterial, fungal, or viral disease.

17. A disease resistant pea plant produced by the method of claim 16.

18. A method of producing a pea pod comprising:
   a) growing the pea plant of claim 2 to produce a pea pod, and
   b) harvesting said pea pod.

19. A method according to claim 18, further comprising processing said pea pod to obtain a berry.

20. A method of producing a berry comprising obtaining a pod of the plant of claim 2 and processing said pod to obtain a berry.

* * * * *